US006432651B1

(12) United States Patent
Hughes et al.

(10) Patent No.: US 6,432,651 B1
(45) Date of Patent: Aug. 13, 2002

(54) METHOD TO DETECT AND ANALYZE TIGHT-BINDING LIGANDS IN COMPLEX BIOLOGICAL SAMPLES USING CAPILLARY ELECTROPHORESIS AND MASS SPECTROMETRY

(75) Inventors: Dallas E. Hughes, Westboro; Barry L. Karger, Newton; James L. Waters, Framingham; Yuriy M. Dunayevskiy, Natick, all of MA (US)

(73) Assignee: Cetek Corporation, Marlborough, MA (US)

( * ) Notice: Subject to any disclaimer, the term of this patent is extended or adjusted under 35 U.S.C. 154(b) by 0 days.

(21) Appl. No.: 09/743,499

(22) PCT Filed: Jul. 9, 1999

(86) PCT No.: PCT/US99/15458

§ 371 (c)(1),
(2), (4) Date: Feb. 26, 2001

(87) PCT Pub. No.: WO00/03240

PCT Pub. Date: Jan. 20, 2000

Related U.S. Application Data

(60) Provisional application No. 60/092,403, filed on Jul. 10, 1998, and provisional application No. 60/094,297, filed on Jul. 27, 1998.

(51) Int. Cl.[7] .......................... C12Q 1/68; G01N 33/53; G01N 33/566
(52) U.S. Cl. .............................. 435/6; 435/7.1; 436/501
(58) Field of Search ........................ 435/6, 7.1; 436/501

(56) References Cited

U.S. PATENT DOCUMENTS

| | | | | |
|---|---|---|---|---|
| 5,114,551 | A | 5/1992 | Hjerten et al. | 204/180.1 |
| 5,228,960 | A | 7/1993 | Liu et al. | 204/182.8 |
| 5,536,382 | A | 7/1996 | Sunzeri | 204/451 |
| 5,783,397 | A | 7/1998 | Hughes et al. | 435/7.1 |
| 6,054,047 | A | * 4/2000 | Hindsgaul et al. | 210/198.2 |
| 6,103,537 | A | * 8/2000 | Ullman et al. | 436/526 |
| 6,299,747 | B1 | * 10/2001 | Dunayevskiy et al. | 204/451 |

FOREIGN PATENT DOCUMENTS

| | | | |
|---|---|---|---|
| EP | 0 572 023 A2 | 5/1993 | |
| WO | WO 96/35946 | 11/1996 | |
| WO | WO 97/22000 | 12/1996 | |

OTHER PUBLICATIONS

Dunayevskiy et al., Rapid Comm. Mass Spectrom. 11(11), 1178–1184 (1997) (Abstract only).*

Yin–Liang Hsieh, et al. "Detection of Noncovalent FKBP–FK506 and FKBP—Rapamycin Complexes by Capillary Electrophoresis—Mass Spectrometry and Capillary Electrophoresis . . . Spectrometry " 8449 Journal of the Amer. Soci. for Mass. Spec. 6 (1995) 85–90.

Oscar–Werner Reif, et al., Fluorescein Isothiocyanate–Labeled Protein G as an Affinity Ligand in Affinity/Immunocapillry Detection Analytical Chemisty 1994, vol. 66, pp. 4025–4033.

Yen–Ho Chu et al., "Affinity Capillary Electrophoresis—Mass Spectrometry for Screening Combinatiorial Libraries", J. Am. Chem. Soc. 1996, vol. 118, pp. 7827–7835.

* cited by examiner

*Primary Examiner*—Kenneth R. Horlick
(74) *Attorney, Agent, or Firm*—Weingarten, Schurgin, Gagnebin & Lebovici LLP

(57) ABSTRACT

This invention combines a capillary electrophoresis (CE) technique for screening complex biological samples with mass spectrometry (MS), to provide a streamlined procedure for identifying and characterizing candidate ligands in a complex biological sample that bind at a selected binding strength to a selected target molecule. The method of the invention advantageously identifies and characterizes tight-binding ligands when high concentrations of weak ligands are present in the sample, which may mask lower concentrations of tight-binding ligands in the sample. The method involves interfacing a capillary from a CE instrument with a post-capillary mass spectrometer to provide direct mass analysis of target/ligand complexes that migrate stably through the CE instrument. All weaker-binding ligands will not be detected during the MS analysis because they dissociate from the target early during the CE run, before reaching and entering the mass spectrometer. Therefore, this method can identify and structurally characterize moderate-to-tight-binding ligands in complex biological samples, even in the presence of high concentrations of weak-binding ligands.

39 Claims, 2 Drawing Sheets

METHOD TO DETECT AND ANALYZE TIGHT-BINDING LIGANDS IN COMPLEX BIOLOGICAL SAMPLES USING CAPILLARY ELECTROPHORESIS AND MASS SPECTROMETRY

CROSS REFERENCE TO RELATED APPLICATIONS

This application claims priority from U.S. Provisional Application Nos. 60/092,403 and 60/094,297, respectively filed on Jul. 10 and Jul. 27, 1998, as well as from International Application No. PCT/US98/27463, filed on Dec. 23, 1998. The entire texts of those applications are herein incorporated by reference.

STATEMENT REGARDING FEDERALLY SPONSORED RESEARCH OR DEVELOPMENT

FIELD OF THE INVENTION

The invention relates generally to methods of screening complex biological materials for effective regulatory, therapeutic, or diagnostic compounds. The invention encompasses using capillary electrophoresis and mass spectrometry together in a method particularly advantageous for detecting and characterizing tight-binding ligands in mixtures that may also include much higher concentrations of competing, weaker-binding ligands. The method also allows ranking of ligands according to their relative binding strengths.

BACKGROUND OF THE INVENTION

Developing screening protocols to identify new, biologically active compounds can present unique and difficult challenges, especially when screening complex materials, particularly a "complex biological sample" (CBS): any sample of material that may have an effect in a biological system. Examples of CBS include but are not limited to: a natural product; a natural extract; a biological preparation; a chemical mixture; a pure compound library; and a combinatorial library.

While capillary electrophoresis has previously been used to detect and/or to analyze known compounds and materials of known composition, this technology has not been widely used, until recently, to screen complex biological samples for target-binding compounds that were previously unknown or unidentified as being ligands to a selected target molecule.

For example, WO 97/22000 encompasses four broad embodiments of a capillary electrophoretic screening method for unknown, biologically active compounds, as follows.

(1) In a non-competitive embodiment of WO 97/22000, a target and complex biological sample are mixed together, then an aliquot of that target/sample mixture is subjected to capillary electrophoresis (CE), and the CE migration of the target is tracked. The target's migration pattern under these conditions are compared against a reference standard, typically the unbound target's migration pattern in the absence of any target-binding ligand.

(2) In a non-competitive, subtractive analysis embodiment of WO 97/22000, a target and sample are mixed together and then subjected to CE. The migration pattern of this mixture is compared to the migration pattern of a sample of the complex biological material alone. Any difference between the two migration patterns suggests the presence in the sample of a hit compound that can bind to the target.

(3) One competitive binding embodiment is provided in WO 97/22000, which tracks known, charged ligand: The target is first mixed with a complex biological material sample and then with a known, charged ligand that binds tightly to the target, to form a sample/target/known ligand mixture. This method uses an essentially equilibrium setting when incubating target and known, tight-binding ligand together, so that the known, tight-binding ligand can displace any weaker-binding hit, prior to CE. This mixture is subjected to capillary electrophoresis and the migration of the known, charged ligand is tracked. (Thus, this method is useful when the target is not easily detected during CE.) Any difference in the known, charged ligand's migration pattern, when in the presence of both the target and a complex biological material sample, from the known ligand's migration pattern when in the presence of the target alone, indicates the presence of a candidate, unidentified target-binding ligand in that sample.

(4) In another competitive binding embodiment of WO 97/22000, the target's migration is tracked and the CE running buffer contains a known, weak-binding, competitive ligand. The target is mixed with a sample, and an aliquot of the mixture is subjected to CE in the presence of a known, relatively weak, target-binding 'competitor' ligand in the CE running buffer. The migration of the target is tracked during CE. The reference standard is the migration of a target plug alone in the known ligand-containing CE buffer, its migration being shifted by its weak, reversible binding to the known ligand dispersed in the CE buffer, as compared to the target's migration alone ligand-free buffer. This competitive screening method can detect a tight-binding hit compound in a target/natural sample mixture, because the hit binds up the target for the entire CE run and prevents the target's interaction with the known weak-binding ligand in the buffer. Therefore, the CE migration pattern of the target in the sample/target aliquot would shift back to the target's migration position as it would be in ligand-free running buffer. This method, too, is particularly useful when the unbound target is not easily detected in ligand-free buffer during CE.

While WO 97/22000 provides useful CE screening methods, they do not overcome some common drug-screening problems. A major obstacle to successful and cost-effective drug screening has been the presence of high concentrations of one or several weak, target-binding ligand compound(s) in a screened sample, which can mask the presence of more valuable, moderate-to-tight-binding or tight-binding ligands occurring at a lower concentration within the same sample. Another major obstacle is obtaining structural information about the high affinity ligands, especially when they are present in very complex mixtures.

Therefore, there remains a need for rapid and cost-effective screening tools for discovering new bioactive and/or potential regulatory compounds that bind to molecules involved in disease or essential molecules of key metabolic pathways. Also needed is a way of characterizing those candidate ligands displaying the highest binding strengths to the target.

BRIEF SUMMARY OF THE INVENTION

The present invention answers these needs by providing an improved screening method combining both capillary electrophoresis and mass spectrometry techniques. Capillary electrophoresis, specifically capillary zone electrophoresis, enables rapid and cost-effective separation and identification of compounds in a sample while consuming only minute amounts of the sample. In the particular application taught here, capillary electrophoresis (CE) enables selective identification of particular candidate ligand(s) that bind(s) tightly to a target of interest. The CE steps are optimized to screen out all but those ligands that bind to the target molecule of interest at or above a selected binding strength, as taught in International Application No. PCT/US98/27463, herein incorporated by reference.

Mass spectrometry (MS) enables analysis of biomolecules, such as peptides and proteins, at the molecular level with high mass measurement accuracy. Suitable MS ionization techniques include, but are not limited to electron impact ionization (EI), electrospray ionization (ESI), chemical ionization (CI), atmospheric-pressure chemical ionization (APCI), matrix-assisted-laser-desorption ionization (MALDI), thermospray (TSP), and fast atom bombardment (FAB) ionization. These ionization techniques may be combined with time-of-flight (TOF), single or triple quadrupole, Fourier transform, or ion trap MS analysis to provide additional information of the compounds analyzed. For example, MALDI-TOF mass spectrometry is valued for ease of sample preparation, predominance of singly charged ions in mass spectra, sensitivity, and high speed. Ion trap and Fourier transform MS allow re-analysis of the ions, as needed. If desired, the ions may be subjected to fragmentation, such as collision-induced dissociation (CID), during mass spectrometry to provide additional structural or substructural data.

Moreover, since MS allows compounds to be detected and differentiated by their molecular weight and/or size, it may be used to observe selectively the target's migration pattern after undergoing CE either alone or in the presence of a complex biological sample. Therefore, MS allows one to eliminate any separate detector and/or any derivatization of the target, if one so desires.

Alternatively, one may use a separate detector, e.g. an ultraviolet absorbance (UV) or fluorescence detector (e.g., light-induced fluorescence (LIF), at a point along the CE capillary or microchip, to track the target's migration during CE, and to generate a CE profile separate from mass spectrometry data.

Identifying and immediately characterizing those candidate ligands that form the most stable complexes with the selected target, minimizes the time and resources needed for isolating and characterizing these compounds. The invention provides a more cost-effective screening protocol since the most stable target-binding ligands are those most likely to be effective therapeutic, regulatory, and/or diagnostic compounds and drugs.

The method generally combines a capillary electrophoresis (CE) technique for screening complex biological samples with a mass spectrometry (MS) analysis step to provide a streamlined procedure for selectively identifying and characterizing any candidate ligand(s) in a complex biological sample that binds at a selected binding strength to a selected target molecule. Advantageously, the CE/MS method can selectively identify and characterizes moderate-to-tight binding ligands (MTLs), especially tight-binding ligands (TLs), even in the presence of high concentrations of weak ligands (WLs) that often mask lower concentrations of tight-binding ligands in the same sample. As a result, the present method improves over prior CE screening methods, by selectively detecting TLs over WLs, and by providing valuable structural data about candidate tight-binding ligands, all in one procedure. Alternatively, as desired, one can adjust the CE and other conditions of the method so that weaker binding ligands are detected. The present method also allows the ranking of target-binding ligands detected in a complex biological sample according to their relative binding strengths.

Mass spectrometric analysis of compounds screened and separated by capillary electrophoresis offers the advantages of rapidly obtaining structural characterization of high-affinity ligands identified by CE. As well, the mass spectrometer itself can be used to track the CE migration of the target, by selectively monitoring the mass/net charge (m/z) ratio of the ionized target, and thus to selectively detect any candidate ligand of a desired binding strength. Using the mass spectrometer as a detector eliminates the need to use any additional detector and the need to label or otherwise derivatize the target to make it detectable during CE.

Specifically, the method involves interfacing a capillary or microfabricated chip of a CE instrument with a post-capillary mass spectrometer. A suitable interface is provided by, e.g, the microscale fluid handling system disclosed in Karger et al., U.S. Pat. No. 5,872,010. The present method provides direct mass and structural analysis of candidate ligands that form target/ligand complexes that migrate stably through the CE instrument, a detectable amount (e.g., at least 50% or at least 80%) of which remains tightly bound, i.e., for a substantial portion of the CE run time, preferably at least 50% or, even better, at least 80%, most preferably until they reach the outlet end of the CE capillary. All weaker-binding ligands will remain undetected during the MS analysis because they substantially dissociate from the target before reaching the outlet end of the capillary and entering the mass spectrometer, preferably early during the CE run. Therefore, the present method can preferentially identify and structurally characterize tight-binding ligands in complex biological samples.

In summary, the present method screens complex biological material for and characterizes any candidate ligand that binds to a selected target at or above a selected binding strength, by the steps disclosed herein.

In one embodiment, a complex biological sample is combined with a selected target to form a sample/target mixture. A plug of the sample/target mixture is then injected into an inlet end of a conduit of a capillary electrophoresis instrument (e.g., a capillary or a channel of a microchip). The compounds within the sample/target plug are subjected to capillary electrophoresis (CE) under predetermined conditions. The predetermined CE conditions have been optimized so that any first complex, formed between the target and any candidate ligand binding to the target at or above a selected binding strength (e.g., a tight binder), remains bound for a substantial part the capillary electrophoresis run time, and so that any additional complex(es), formed between the target and any additional ligand(s) binding to the target below the selected binding strength (e.g. a weak binder), dissociates prior to reaching the CE/MS interface at the outlet end of the CE conduit. In at least one embodiment, the migration of the target during capillary electrophoresis is tracked, enabling one to obtain at least one capillary electrophoretic profile of the sample/target plug. The target's migration may be tracked by, e.g., an ultraviolet light absorbance or fluorescence detector coupled to the CE capillary. Alternatively, on-line MS detection can be used exclusively, obviating the need for absorbance or fluorescence detection. The compounds from the electrophoresed sample/target plug are introduced from the capillary electrophoresis instrument into an on-line mass spectrometer interfaced with the CE instrument. The compounds from the electrophoresed sample/target plug are subjected to ionization and then mass spectrometry analysis (i.e., the mass spectra of the ions are analyzed). The mass spectrometry data are gathered.

One obtains and analyzes the CE profile of the sample/target and target plugs, i.e., the migration pattern of the unbound or bound target upon capillary electrophoresis. One may look at either a time shift in the target's migration peak, resulting from it being bound by a moderate-to-tight-binding ligand. Alternatively, particularly if using fluorescence or absorbance detection, or single-ion monitoring during MS, one can look at other parameters, such as the shape, area, or size of the unbound target peak and/or any bound target/ligand complex peak(s) detected, and any change(s) in at least one of those parameters.

One analyzes at least one capillary electrophoretic profile generated from the present CE/MS screening method (from the absorbance, fluorescence, or MS data), by comparing it to at least one reference standard. From that comparison, one determines whether the capillary electrophoretic profile indicates the presence of a candidate target-binding ligand, typically but not necessarily an unidentified one, in the complex biological sample. As well, the mass spectrometry data of the ionized sample/target compounds are analyzed to determine the mass and other structural data of any detected target-binding ligand, including a candidate ligand having the desired binding strength. Structural data may be provided by performing collision-induced dissociation (CID) mass spectrometry or other appropriate fragmentation process, e.g., post-source decay, in-source fragmentation, etc.

DETAILED DESCRIPTION OF THE INVENTION

The method of the invention allows on-line identification and characterization of candidate ligand(s) present in a complex biological sample that can bind to a selected target at a selected binding strength. For instance, tight-binding ligands can be detected preferentially even in the presence of high concentrations of weaker-binding ligands. The candidate ligand is often one that was previously unidentified as a ligand to the target. Characterization of any candidate ligand detected includes determination of its mass data.

Figure 1:
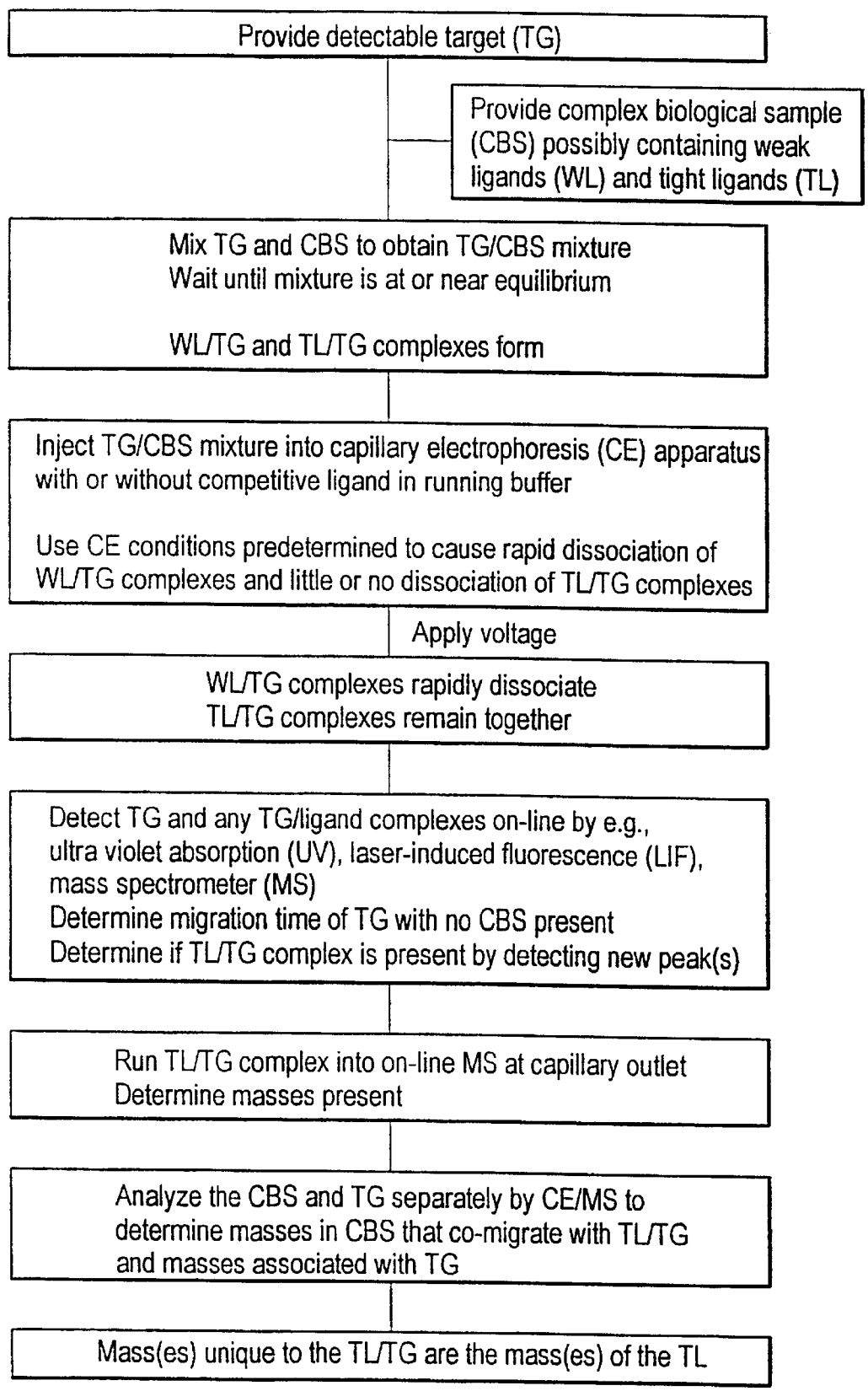
FIG. 1 is a flow diagram depicting the general method of the invention.
Figure 2:
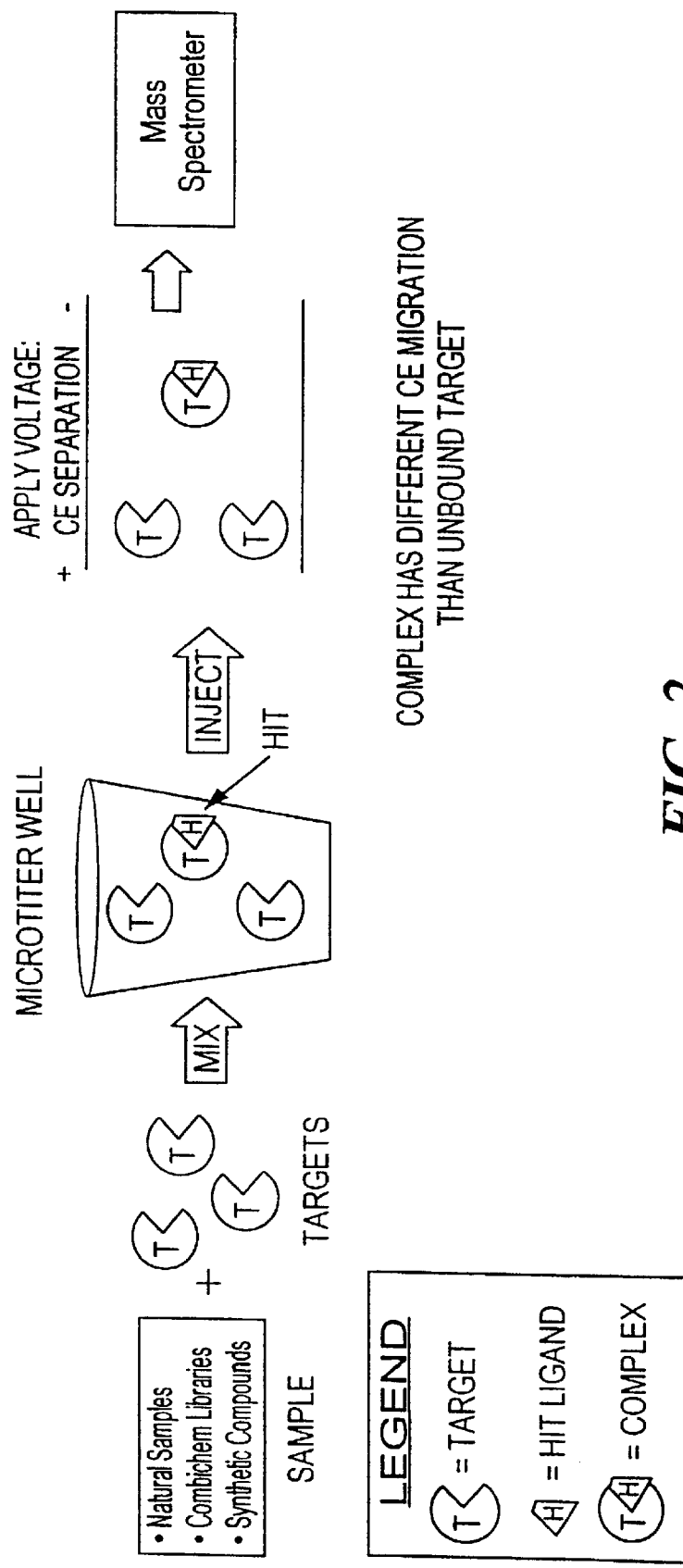
FIG. 2 is a schematic representation of the capillary electrophoretic assay screening method of the invention.

The invention is described with reference to the flow diagram of FIG. 1, which summarizes the method generally. FIG. 2 illustrates pictorially the method of the invention in general.

In one embodiment of the invention, the target (TG) is first mixed with the complex biological sample (CBS) to be screened. A target molecule (TG) used in-, the present method may be, for example, a protein or nucleic acid involved in a disease process or a protein or gene to be regulated in a physiological setting. Examples of "complex biological samples" (CBS) include but are not limited to: naturally occurring samples, products or extracts; various biological preparations; chemical mixtures; libraries of pure compounds; and combinatorial libraries of synthetic compounds. Examples of natural extracts include extracts of terrestrial plants; extracts of marine plants; extracts of marine organisms; microbial broths; and microbial extracts.

The TG will form complexes with any binding ligand(s) present in the sample, including weak-binding ligands (WLs), moderate-to-tight binding ligands(MTL), and tight-binding ligands (TLs). After an incubation period, a plug of the sample/target (CBS/TG) mixture is then injected into a capillary in a capillary electrophoresis instrument and voltage is applied so as to subject the compounds of the injected plug to CE.

The electrophoretic conditions affect the stability of weak and strong ligand/target complexes to different degrees. Therefore, one can set the CE conditions so that weak ligand/target complexes will substantially dissociate during the CE so that any weak ligand/target complexes remaining will be below the particular detector's detection limits. At the same time, the CE conditions should allow tight-binding ligand/target complexes to remain present at a level above the detection limits of the detector.

In order to practice the present on-line CE/MS screening process successfully, all CE conditions (e.g., temperature, column length) must be optimized to detect ligand compounds having an affinity or binding strength for the selected target at or above a desired threshold, as will be appreciated by one of ordinary skill in capillary electrophoresis in view of the teachings of this disclosure together with International Application no. PCT/US98/27463. One must define, in a given set of CE conditions, what are weaker-binding ligands (WLs) and tight-binding ligands (TLs) in terms of the amount or percentage of complexes remaining bound, the extent or length of time that the ligand and target stay complexed together during CE, and/or changes in the shape or size of the bound and unbound target peaks.

Factors governing the relative binding strength of a ligand to a target include, but are not limited to: capillary length; the distance between the CE starting point and the detector; CE run time; voltage and temperature during CE; and buffer composition, such as its pH and/or salt concentration. Generally for the method, buffer pH values may be within the range of about pH 3 to about pH 10; CE voltages may be about 5–30 kV; and salt concentrations may be within the range of about 0–100 mM.

The CE conditions are experimentally predetermined prior to carrying out the CE/MS screening method. That is, one can establish the exact running buffer(s), temperature, voltage, and other CE conditions by using known WLs and TLs, and/or by generally usually known guidelines regarding interactions between particular types of molecules (e.g., protein-protein, protein-DNA. etc.).

Typically, the conditions are set so that WLs have high off-rates and substantially dissociate from the target (TG) before reaching the outlet end of the CE conduit and entering the mass spectrometer, preferably early in the CE run. Conversely, TLs typically have low off-rates and stay bound to the target for sufficient time during CE and in an adequate amount so as to shift the target's CE profile or pattern detectably (whether in terms of a time shift or change in peak shape or size), whether detection is by post-CE MS or by an absorbance or fluorescence detector during CE. The CE conditions are preferably such that a detectable amount of TL remains bound to the target for a substantial part of the CE run time, preferably at least 50%, preferably at least 80%, most preferably for substantially the entire CE run so that the TL/TG complex reaches the outlet end of the CE conduit.

As has been noted, the method of the invention is particularly advantageous in identifying and characterizing, in a screened sample, candidate ligand compound(s) having a binding strength higher than a selected threshold and for determining their relative binding strengths. "Weak-binding" ligands typically have faster off-rates ($K_{off}$) and higher dissociaton constants ($K_d$), and form target/ligand complexes that are unstable and fall apart relatively quickly before reaching the outlet end of a CE conduit such as a capillary or microchip channel. In contrast, "tight-binding" ligands have lower $K_d$ and slow off-rates ($K_{off}$), forming target/ligand complexes, a substantial amount of which remains bound for a substantial portion of the CE run, preferably at least until the outlet end of the capillary. "Moderate-binding" ligands will have intermediate $K_d$ and $K_{off}$ values. Exemplary criteria for defining ligands of a relative binding strength are shown in Table 1.

TABLE 1

| Ligand | Approx. $K_D$ range | Approx. $K_{off}$ range | Functional Definition |
|---|---|---|---|
| Tight-binding (TL) | <1.0 μM; preferably ≦10 nM | <1.0 (s$^{-1}$); preferably ≦0.01 (s$^{-1}$) | A detectable amount of the TL/TG complex remains bound for a substantial part, at least 50%, of the capillary electrophoresis run, wherein a detectable amount is that amount of TL/TG complex that is above the lower detection limit of the absorbance or fluorescence detector and/or mass spectrometer. |
| Moderate-binding (ML) | 1.0–100 μM | 1.0–10(s$^{-1}$) | A substantial amount, preferably at least 50%, of ML/TG or WL/TG complexes dissociates before reaching the outlet end of the CE capillary or channel, preferably within the first 20% of the CE run, so that any remaining WL/TG complex that reaches the mass spectrometer is below the lower detection limit of the absorbance or fluorescence detector and/or mass spectrometer. |
| Weak-binding (WL) | >100 μM | >10.0 (s$^{-1}$) | |

Other functional definitions of tight versus moderate-to-weak binding ligands may be determined by how they respectively affect or modulate the shape of the target's migration peak, e.g., by reducing the area of the unbound target peak and/or by producing a new bound target/ligand complex peak. For example, a functional definition of a tight-binding ligand may be one that forms a target/ligand complex of which a detectable amount holds together during CE so that the complex's dissociates by no more than 50% after about 1.5–5.0 minutes into a CE run. Conversely, a weak-binding ligand would then be one that forms a target/ligand complex of which a substantial amount, at least 50% and preferably at least 80%, dissociates during CE so that the complex's migration peak is reduced by at least 90% after about 1.5–5.0 minutes into a CE run.

Once the CE conditions are chosen, the screening method itself uses the fact that the rate of ligand/target complex dissociation is different for weak-binding ligands and tight-binding ligands. Therefore, using optimized CE conditions, one can achieve complete dissociation of weak ligand/target complexes, or at least enough dissociation so that any remaining weak ligand/target complex falls below the threshold for detection during CE. On the other hand, the tight-binding ligand/target complex may dissociate to some degree, but sufficient TL/TG complex must remain to be at a concentration above the detection limits of the particular detector. For instance, a mass spectrometer's detection limit is typically within the range of about 100 nM–100 uM of a compound. Therefore, aside from the unbound target signal or peak, the only other distinctive signal(s) that would be detected would be any signal due to the shifted CE migration or mobility of the target when bound to a tight-binding ligand. One of ordinary skill in capillary electrophoresis will be able to determine, in light of this disclosure, how to distinguish between weak and tight-binding ligands to a selected target, depending on the particular CE conditions and the particular detection limits.

This method allows one to determine whether one or more tight-binding ligand(s) is/are present in the biological sample even in the presence of high concentrations of weak ligands. This fact will hold true as long as the tight-binding ligand/target complex is formed in the pre-capillary incubation step of a complex biological sample with a target in a concentration above the detection limits of the detector used to track the migration of the target. The detector may be, for example, a UV absorbance detector or a laser-induced fluorescence (LIF) located along the length of the CE conduit, preferably near the outlet end of the conduit, or may be the mass spectrometer itself.

After voltage is applied to the CE capillary or microchip, and as the target (TG) begins to migrate through the capillary, any weak-binding ligand/target (WL/TG) complex should rapidly dissociate and the TG should migrate essentially as unbound TG. Any candidate tight-binding ligand/target (TL/TG) complex that forms must remain largely intact, with a substantial amount of the complex staying bound together for a substantial portion of the CE run time, at least approximately 50% and more preferably, approximately at least 80%. That is, enough of the TL/TG complex must remain together for a sufficient time during CE so as to be detectable during MS.

Additionally, the method of the invention may be practiced with or without a known, charged, preferably weak-binding, competitive ligand (CL) in the CE running buffer (RB), the CL serving to change the CE migration time of the target as it moves through this buffer. An exemplary known charged competitive ligand is one that binds weakly to the target and has a dissociation constant ($K_d$) greater than 1.0 μM and an off-rate ($K_{off}$) greater than 1.0 (s$^{-1}$).

For instance, if a candidate TL happens to be neutrally charged, a new TL/TG complex peak may not be detected in running buffer free of CL as the complex's migration may not shift from that of unbound target. The neutral TL's presence may be detected only by including a known, charged, preferably weak-binding, CL in the running buffer. The target bound by the neutral, tight-binding candidate ligand would not be able to interact with the CL, so that the target's migration rate through the CL-containing running buffer would no longer be shifted by the CL but would revert back towards a migration rate of the target alone when in running buffer free of CL.

If the candidate TL is charged, a new TL/TG peak should be detected whether or not the CL is present in the running buffer, unless the TL has the same charge as the CL so that the TL shifts the target's migration to the same extent as the CL. In the latter case, two CE runs of the sample/target plug may be desired, one with and one without CL in the running buffer, to establish unequivocally the presence in the CBS of a candidate ligand having the desired binding strength.

When the method is practiced with a known, charged competitive ligand in the running buffer, determining the presence of a candidate ligand comprises comparing the sample/target plug's capillary electrophoretic profile in that buffer with a reference standard comprising a capillary electrophoretic profile of the target in running buffer free of any target-binding ligand and a capillary electrophoretic profile of the target in running buffer that includes the known, charged competitive ligand. Determining the mass and/or structure of the candidate ligand will be simplified if the mass spectra of the known competitive ligand is known and can be used as a reference standard in addition to the mass spectra of the target alone.

Detection of the target and stable ligand/target complexes can be performed by several well-established detection methods, including but not limited to UV light absorbance, laser-induced fluorescence (LIF), or on-line MS. Tracking the migration of the target produces a capillary electrophoretic profile or migration pattern, which can be analyzed to determine whether the screened CBS contains any ligand capable of binding to the target at a selected binding strength.

Any MS ionization technique may be used, including: electron ionization (EI); electrospray ionization (ESI); matrix-assisted laser desorption ionization (MALDI); chemical ionization (CI); atmospheric pressure chemical ionization (APCI); and thermospray ionization (TSI).

The mass spectrometer may be configured for time-of-flight (TOF) mass spectrometry, single-quadrupole mass spectrometry, triple-quadrupole mass spectrometry, Fourier transform mass spectrometry, or fast atom bombardment (fab) mass spectrometry. Especially preferred are MS techniques enabling high through-put of samples.

The on-line CE/MS set-up allows one to detect the target's CE migration pattern by MS data alone, if so desired, as can be appreciated by one of ordinary skill in the art in view of the teachings of this disclosure. For instance, one can use single-ion monitoring to track the target's CE mobility through its m/z (mass/net charge) ratio. The CE profile of the target can be provided by mass spectrometry data because a plug of unbound target has a different CE mobility from that of a target tightly bound to a charged ligand. Therefore, after CE, unbound target and target that has been bound tightly to a ligand will arrive at and enter the mass spectrometer at respectively different times. As a result, there will be different peaks or distributions in the mass data occurring at different times, which will correspond to unbound TG, to TG that has been complexed to TL, and to the TL. As well, the size or area of each peak may differ and changes can be monitored. One can monitor the target alone, observe its location and compare its mass spectra in relation to its time of arrival, and then compare these data to the MS data for a mixture of target and ligand.

One advantage of using the mass spectrometer as the sole detector is that it eliminates the need for labelling or derivatizing the target molecule to make it detectable. As well, the mass spectrometer allows a certain selectivity in looking for candidate ligands that bind at or above a desired binding strength. A mass spectrometer is a particularly useful detector when using a known, charged competitive ligand (CL) in the CE running buffer, since the mass spectra of the target and any other target-binding ligand will not be affected by the CL.

Moreover, if one detects a tight-binding ligand/target (TL/TG) complex via on-line MS, the TL/TG complex can then be directly analyzed by the mass spectrometer. Once the TL/TG complex is ionized, the complex may break apart or stay together. In either case, the individual ion masses are determined in the mass spectrometer. If detection is by another method, such as light absorbance detection (e.g., ultraviolet (UV) absorbance) or fluorescence detection (e.g., laser-induced fluorescence (LIF) detection), one must still interface the CE instrument with a mass spectrometer and determine the masses associated with the TL/TG complex, as discussed before.

Two CE/MS control runs must be performed. The first is performed with complex biological sample alone, to determine those components in the CBS that co-migrate with the TL/TG complex. The second is performed with TG alone to determine any masses that are associated with the TG. By subtractive analysis of the data from the one experimental CE/MS run of a plug of the sample/target mixture, and from the two control runs, one then determines the mass(es) of the TL(s).

If the complex biological sample is composed of a mixture of compounds of known masses, such as mixtures of synthesized compounds, a single MS analysis may be enough to completely identify the compound. Sometimes it may be necessary to re-analyze the ions in the mass spectrometer to obtain additional structural information about the TL. Such re-analysis is possible if one uses, e.g. an ion trap mass or Fourier Transform mass spectrometer.

Additionally, the method may further comprise subjecting the electrophoresed sample/target compounds to collision-induced dissociation (CID) during mass spectrometry to generate CID data about the target, any detected candidate ligand, or both. This method is useful to detect the structure and molecular weight of unknowns, such as may be found in natural products. This step is particularly useful for differentiating compounds having the same molecular weight, by the fragmentation behaviors of the ions upon CID. For instance, CID analysis is helpful when screening for a candidate target-binding ligand among a library of known compounds having known molecular weights. Analyzing CID data of an electrophoresed sample/target plug allows one to identify and to determine the structure of any candidate ligand detected.

Therefore, the invention provides a method of screening complex biological material for and characterizing any candidate ligand that binds to a selected target at or above a selected binding strength. Generally, one embodiment of the method comprises the steps of:

(1) providing a complex biological sample;
(2) combining the complex biological sample with the selected target to form a sample/target mixture;
(3) injecting a plug of the sample/target mixture from step (2) into an inlet end of a conduit of a capillary electrophoresis instrument;
(4) subjecting compounds within the sample/target plug to capillary electrophoresis under predetermined conditions,
   wherein the conditions are optimized so that a detectable amount of any first complex formed between the target and any candidate ligand binding to the target at or above a selected binding strength, remains bound for a substantial part of the capillary electrophoresis run, and
   wherein the conditions are optimized so that a substantial amount of any additional complex(es) formed between the target and any additional ligand(s) binding to the target below the selected binding strength, dissociates before reaching the outlet end of the conduit;

(5) introducing the electrophoresed sample/target compounds from the capillary electrophoresis instrument into an on-line mass spectrometer interfaced with the capillary electrophoresis instrument;

(6) subjecting the electrophoresed sample/target plug compounds to ionization in the mass spectrometer;

(7) obtaining a capillary electrophoretic profile of the sample/target plug and determining whether the sample/target plug's profile indicates the presence of a candidate ligand in the complex biological sample; and (8) using mass spectrometry data from step (6) to determine a mass of any candidate target-binding ligand detected.

The whole process can be performed in a capillary or on a microfabricated chip having a plurality of channels, into which plugs of sample/target mixture can be injected for capillary electrophoresis prior to MS.

A "capillary electrophoretic profile" is the migration pattern obtained by tracking the target upon capillary electrophoresis of, e.g., a plug of target alone or a sample/target plug. The target's migration may be tracked by various detection means, including a fluorescence or absorbance detector or a mass spectrometer.

A "candidate ligand" is one that binds tightly to the selected target at or above a selected binding strength, preferably a tight-binding ligand.

A "detectable amount of the first complex" is that amount of candidate ligand/target complex that is above the lower detection limit of the particular detector used, especially the mass spectrometer. Generally at least approximately 50%, more preferably at least approximately 80%, of the first complex remains bound for a substantial part of the capillary electrophoresis run time. The "substantial portion of the capillary electrophoresis run time" is at least approximately 50%, and more preferably at least approximately 80% of the entire duration of the CE run.

The "substantial amount of any additional complex" of any additional, weak-binding ligand and target that dissociates, is such that the amount of any remaining additional complex that reaches the mass spectrometer is below the mass spectrometer's lower detection limit. Preferably, at least 50%, more preferably at least 80%, of any additional complex(es) detected dissociate(s) before reaching the outlet end of the capillary electrophoresis conduit. Especially advantageous CE conditions are those that enable a detectable amount of the first complex to remain substantially intact for the entire capillary electrophoresis run while at least 50% of any additional complex(es) of a weaker-binding ligand(s) and target dissociate(s) within the first 20% of the capillary electrophoresis run time.

The sample/target plug's capillary electrophoretic profile may be obtained by tracking the target's migration at a detection point along a length of the conduit, by means of, e.g., a light absorbance detector or a fluorescence detector. Alternatively, the sample/target plug's CE profile may be provided by the post-capillary mass spectrometry data.

Determining the presence, in the complex biological sample, of a candidate target-binding ligand having the requisite binding strength, comprises comparing the sample/target plug's capillary electrophoretic profile with a reference standard comprising a capillary electrophoretic profile of a plug of the target in the absence of any target-binding ligand. Determining the mass of any detected candidate ligand comprises comparing mass spectrometry data (mass spectra) of the electrophoresed sample/target compounds to a reference standard comprising mass spectrometry data of a capillary electrophoresed plug of the target alone and mass spectrometry data of a capillary electrophoresed plug of complex biological sample alone. Determining the structure of any detected candidate ligand may entail comparing not only the mass spectra of various compounds, including the target and various ligands, but also comparing the fragmentation data (e.g., collision-induced dissociation data) of the electrophoresed sample/target compounds to a reference standard comprising fragmentation data of the target alone in the absence of any target-binding ligand and/or fragmentation data of the target together with a known target-binding ligand.

Finally, one may vary the method's CE conditions (e.g., temperature, buffer composition, voltage, etc.), as taught in International Application No. PCT/US98//27463, so as to affect the relative off-rates of a number of target-Binding ligands and thereby determine their relative binding strengths. Particularly with respect to small molecules, e.g., many drug-like compounds, their CE off-rates correlate to their relative binding strengths. Small molecules are approximately $\leq 1000$ daltons in size. Therefore, the present method can be used to rank candidate ligands according to their relative affinities for a selected target and thus, their potential value as therapeutic or diagnostic compounds.

Another embodiment of the CE/MS screening method of the invention may be practiced to detect and to characterize moderate-binding ligands that may not be as easily detected in the previously discussed embodiments. In this case, a CE running buffer is made up that includes the complex biological sample (e.g., a mixture of synthetic compounds that are potential ligands to a selected target). A plug of target is injected into and electrophoresed in a CE conduit filled with this CBS-containing running buffer. As the target migrates through this buffer, the target is able to bind to any target-binding ligands present in the CBS. In this set-up, any potential target-binding ligand(s) tend(s) to be present in higher concentrations, as compared to the previous embodiment in which the target and CBS are first mixed together and then a plug of that mixture is injected into the CE conduit (i.e., where the running buffer does not include CBS). Therefore, moderate-to-weak ligands are then better able to stay bound to the target and thus to be detected.

Generally, then, the steps of this embodiment, having CBS in the running buffer, comprise:

(1) injecting a plug of a target alone into an inlet end of a conduit of a capillary electrophoresis instrument, the conduit being filled with a running buffer comprising a complex biological sample;

(2) subjecting compounds within the sample/target plug to capillary electrophoresis under predetermined conditions, wherein the conditions are optimized so that a detectable amount of any first complex formed between the target and any candidate ligand binding to the target at or above a selected binding strength, remains bound for a substantial portion of the capillary electrophoresis run time, and wherein the conditions are optimized so that a substantial amount of any additional complex(es) formed between the target and any additional ligand(s) binding to the target below the selected binding strength, dissociates before reaching the outlet end of the conduit;

(3) introducing the electrophoresed sample/target compounds from the capillary electrophoresis instrument into an on-line mass spectrometer interfaced with the capillary electrophoresis instrument;

(4) subjecting the electrophoresed sample/target plug compounds to ionization and mass spectrometry analysis;

(5) obtaining a capillary electrophoretic profile of the sample/target plug and determining whether the sample/target plug's profile indicates the presence of a candidate ligand in the complex biological sample; and
(6) using mass spectrometry data from step (4) to determine a mass of any candidate target-binding ligand detected.

The data collected from this screening method will be compared to reference standards comprising the CE profile and mass spectrometry data from a target plug alone electrophoresed in buffer free of CBS, and/or mass spectrometry data from CBS alone.

EXAMPLE I

The method of the invention is particularly advantageous for screening a split-and-pool combinatorial library. This library is a mixture of synthetic compounds containing anywhere from several tens to several thousands of compounds of known masses. Often, many of these compounds have weak binding activity, i.e., are weak-binding ligands (WLs). They are also frequently present at very high concentrations, in total. It is desirable, but difficult, to find the rare combinatorial derivative compounds in the library that are tight-binding ligands (TLs). In other screening methods, the excess WLs sometimes mask a single TL species that is present at a much lower concentration. The present method, by using MS in conjunction with optimized CE conditions, not only detects such a rare TL, but also identifies its mass and sometimes its substructure as well (through ion fragmentation, such as by collision-induced dissociation during MS). Using this information, one may be able to directly determine, without further steps, which component of the original combinatorial library is the TL.

In contrast, using other screening methods, once an active split-and-pool library is identified (i.e., one that contains a potential target-binding ligand), one would need to deconvolute it—in other words, re-synthesize and re-screen the library in several different combinations, or retest all the compounds individually. Alternatively, one would need to perform lengthy fractionation and analysis steps to determine if the combinatorial library contains TLs and t hen to identify the actual TLs. The present on-line CE/MS screening method eliminates or substantially reduces the need to perform such complex procedures and analyses.

While the present invention has been described in conjunction with preferred embodiments, one of ordinary skill in the art, after reading the foregoing specification, will be able to effect various changes, substitutions of equivalents, and other modifications to the methods and compositions set forth herein.

What is claimed is:

1. A method of screening complex biological material for and characterizing any candidate ligand that binds to a selected target at or above a selected binding strength, the method comprising the steps of:
   (1) providing a complex biological sample;
   (2) combining the complex biological sample with a predetermined concentration of the selected target to form a sample/target mixture;
   (3) injecting a plug of the sample/target mixture from step (2) into an inlet end of a conduit of a capillary electrophoresis instrument;
   (4) subjecting compounds within the sample/target plug to capillary electrophoresis under first predetermined conditions,
      wherein the first predetermined conditions are optimized so that a detectable amount of any complex(es) formed between the target and any candidate ligand(s) binding to the target at or above a first selected binding strength, remains bound for a substantial portion of the capillary electrophoresis run time, and
      so that a substantial amount of any additional complex(es) formed between the target and any additional ligand(s) binding to the target below the selected binding strength, dissociates before reaching the outlet end of the conduit;
   (5) introducing the electrophoresed sample/target compounds exiting from the capillary electrophoresis instrument into an on-line mass spectrometer interfaced with the capillary electrophoresis instrument;
   (6) subjecting the electrophoresed sample/target plug compounds to ionization and mass spectrometry analysis;
   (7) examining a capillary electrophoretic profile of the sample/target plug, the capillary electrophoretic profile having been generated either by tracking the target's migration during capillary electrophoresis in step (4) or by mass spectrometry analysis in step (6), and determining whether the sample/target plug's profile indicates the presence of a candidate ligand in the complex biological sample;
   (8) using mass spectrometry data from step (6) to determine a mass of any candidate target-binding ligand detected; and
   (9) repeating steps (3)–(8) at least once, wherein each repeat of step (4) is performed under other predetermined conditions that differ from the first predetermined conditions and from predetermined conditions in any other repeat of step (4), and wherein the other predetermined conditions are optimized for detecting candidate ligands binding to the target at a selected binding strength different from the first selected binding strength and from a selected binding strength in any other repeat of step (4).

2. A method of screening complex biological material for and characterizing any candidate ligand that binds to a selected target at or above a selected binding strength, during capillary electrophoresis, the method comprising the steps of:
   (1) injecting a plug of a target alone into an inlet end of a conduit of a capillary electrophoresis instrument, the conduit being filled with a running buffer comprising a complex biological sample;
   (2) subjecting the target plug to capillary electrophoresis under first predetermined conditions,
      wherein the first predetermined conditions are optimized so that a detectable amount of any complex(es) formed between the target and any candidate ligand(s) binding to the target at or above a selected binding strength, remains bound for a substantial portion of the capillary electrophoresis run time, and
      so that a substantial amount of any additional complex(es) formed between the target and any additional ligand(s) binding to the target below the selected binding strength, dissociates before reaching the outlet end of the conduit;
   (3) introducing the electrophoresed target and any target-binding candidate ligand that exit from the capillary electrophoresis instrument into an on-line mass spectrometer interfaced with the capillary electrophoresis instrument;
   (4) subjecting the electrophoresed sample/target plug compounds to ionization and mass spectrometry analysis;

(5) obtaining a capillary electrophoretic profile of the electrophoresed target and any target-binding candidate ligand and determining whether the capillary electrophoretic profile indicates the presence of at least one candidate ligand in the complex biological sample; and
(6) using mass spectrometry data from step (4) to determine a mass of any candidate target-binding ligand detected.

3. The method of claim 1 or 2, wherein the capillary electrophoretic profile is obtained by tracking the target's migration at a detection point along a length of the conduit.

4. The method of claim 3, wherein an ultraviolet absorbance detector or a fluorescence detector is used to track the target's migration during capillary electrophoresis.

5. The method claim 1 or 2, wherein the capillary electrophoretic profile is provided by the mass spectrometry data.

6. The method of claim 1 or 2, wherein determining the presence of a candidate ligand in the complex biological sample comprises comparing the capillary electrophoretic profile with a reference standard comprising a capillary electrophoretic profile of a plug of the target in the absence of any target-binding ligand.

7. The method of claim 1 or 2, wherein determining the mass of a candidate ligand comprises comparing mass spectrometry data of the electrophoresed target and any detected target-binding candidate ligand to a reference standard comprising mass spectrometry data of a capillary electrophoresed plug of the target alone and mass spectrometry data of a capillary electrophoresed plug of complex biological sample alone.

8. The method of claim 1 or 2, which uses a capillary electrophoresis running buffer that includes a known charged competitive ligand that binds to the target and has a dissociation constant ($K_d$) greater than 1.0 $\mu$M and an off-rate ($K_{off}$) greater than 1.0 ($s^{-1}$).

9. The method of claim 8, wherein determining the presence of a candidate ligand comprises comparing the capillary electrophoretic profile of the target and any detected target-binding candidate ligand with a reference standard comprising a capillary electrophoretic profile of the target in running buffer free of any target-binding ligand and a capillary electrophoretic profile of the target in running buffer including the known, charged competitive ligand.

10. The method of claim 1 or 2, further including repeating at least steps (3)–(6), wherein a first performance of the capillary electrophoresis steps uses a capillary electrophoresis running buffer free of any target-binding ligand but the repeat of the capillary electrophoresis steps uses a capillary electrophoresis running buffer that includes a known charged competitive ligand that binds to the target and has a dissociation constant ($K_d$) greater than 1.0 M and an off-rate ($K_{off}$) greater than 1.0 ($s^{-7}$).

11. The method of claims 10, wherein determining the presence of a candidate ligand comprises comparing the capillary electrophoretic profile with a reference standard comprising a capillary electrophoretic profile of the target in running buffer free of any target-binding ligand and a capillary electrophoretic profile of the target in running buffer including the known, charged competitive ligand.

12. The method of claim 1 or 2, wherein the ionization technique is selected from the group consisting of: electron impact ionization (EI); electrospray ionization (ESI); chemical ionization (CI); atmospheric pressure chemical ionization (APCI); matrix-assisted laser desorption ionization (MALDI); thermospray ionization (TSI); and fast atom bombardment (fab) ionization.

13. The method of claim 1 or 2, wherein the mass spectrometer is configured for time-of-flight (TOF) mass spectrometry, single-quadrupole mass spectrometry, triple-quadrupole mass spectrometry, Fourier transform mass spectrometry, or ion trap mass spectrometry.

14. The method of claim 1 or 2, further comprising subjecting the electrophoresed sample/target compounds to fragmentation during mass spectrometry to generate fragmentation data about the target, any detected candidate ligand, or both.

15. The method of claim 14, wherein the fragmentation is achieved by collision-induced dissociation (CID).

16. The method of claim 14, wherein the fragmentation data is used to identify and to determine the structure of any candidate ligand detected, by comparing the fragmentation data of the electrophoresed sample/target compounds to a reference standard comprising fragmentation data of the target alone in the absence of any target-binding ligand.

17. The method of claim 14, wherein the fragmentation data is used to identify and to determine the structure of any candidate ligand detected, by comparing the fragmentation data of the electrophoresed sample/target compounds to a reference standard comprising fragmentation data of the target together with a known target-binding ligand.

18. The method of claim 1 or 2, further comprising subjecting the ionized compounds to additional mass spectrometric analysis.

19. The method of claim 1 or 2, wherein, in at least one capillary electrophoresis step, the capillary electrophoretic conditions are optimized to detect any candidate ligand that binds tightly to the target and has a dissociation constant ($K_d$) less than approximately 1 M and an off-rate ($K_{off}$) less than approximately 1.0 ($s^{-1}$) when in complex with the target.

20. The met-hod of claim 1 or 2, wherein the capillary electrophoretic conditions are optimized to detect any candidate ligand that binds tightly to the target and has a dissociation constant ($K_d$) of approximately 10 nM or less and an off-rate ($K_{off}$) of approximately 0.01 ($s^{-1}$) or less when in complex with the target.

21. The method of claim 1 or 2, wherein the complex biological staple is selected from the group consisting of: a chemical mixture; a pure compound library; a combinatorial library of synthetic compounds; a natural product; a natural extract; and a biological preparation.

22. The method of claim 1 or 2, wherein the target is selected from the group consisting of a protein, a peptide, an amino acid, a nucleic acid, an oligonucleotide, and a pharmaceutical compound.

23. The method of claim 8, wherein the known, charged competitive ligand is selected from the group consisting of a natural compound, a synthetic compound, an antibody, and a pharmaceutical compound known to bind to the target of interest.

24. The method of claim 1 or 2, wherein a detectable amount of the first complex is that amount of candidate ligand/target complex that is above the lower detection limit of the mass spectrometer.

25. the method of claim 1 or 2, wherein at least approximately 50% of the first complex remains bound for the capillary electrophoresis run time.

26. The method of claim 1 or 2, wherein approximately at least 80% of the first complex remains bound for the capillary electrophoresis run time.

27. The method of claim 1 or 2, wherein the substantial amount of any additional complex that dissociates is such that the amount of any remaining additional complex that reaches the mass spectrometer is below the mass spectrometer's lower detection limit.

28. The method of claim 1 or 2, wherein at least approximately 50% of any additional complex dissociates before reaching the outlet end of the capillary electrophoresis conduit.

29. The method of claim 1 or 2, wherein at least approximately 80% of any additional complex dissociates before reaching the outlet end of the capillary electrophoresis conduit.

30. The method of claim 1 or 2, wherein the substantial portion of the capillary electrophoresis run time is at least approximately 50%.

31. The method of claim 1 or 2, wherein the substantial portion of the capillary electrophoresis run time is at least approximately 80%.

32. The method of claim 1 or 2, wherein the detectable amount of the first complex remains substantially intact for the entire capillary electrophoresis run while at least approximately 50% of any additional complex dissociates within approximately the first 20% of the capillary electrophoresis run time.

33. The method of claim 1 or 2 wherein the capillary electrophoresis conditions are optimized to detect a tight-binding candidate ligand having a dissociation constant ($K_d$) of approximately 1 $\mu$M or less and an off-rate ($K_{off}$) of approximately 1.0 ($s^{-1}$) or less, which forms a candidate ligand/target complex whose capillary electrophoretic migration peak area decreases by no more than approximately 50% after approximately 1.5–5.0 minutes of capillary electrophoresis.

34. The method of claim 2, further comprising:

(7) repeating steps (1)–(6) at least once, wherein each repeat of step (2) is performed under other predetermined conditions that differ from the first predetermined conditions and from predetermined conditions in any other repeat of step (2), wherein the other predetermined conditions are optimized for detecting candidate ligands binding to the target at a selected binding strength different from the first selected binding strength and from a selected binding strength in any other repeat of step (2).

35. The method of claim 1 or 34, wherein the predetermined conditions are varied by using a different temperature at which to perform each capillary electrophoresis run.

36. The method of claim 1 or 34, wherein the predetermined conditions are varied by varying, for each capillary electrophoresis run, the composition of a running buffer used to perform the capillary electrophoresis.

37. The method of claim 36, wherein the running buffer's salt concentration differs in each capillary electrophoresis run.

38. The method of claim 36, wherein the running buffer's pH differs in each capillary electrophoresis run.

39. The method of claim 1 or 34, wherein the predetermined conditions are varied by varying, for each capillary electrophoresis run, a voltage at which the capillary electrophoresis is performed.

* * * * *